United States Patent [19]

Hurt et al.

[11] 4,201,693

[45] May 6, 1980

[54] STABLE SCHIFF REAGENT

[75] Inventors: Wesley D. Hurt, Philadelphia, Pa.; John P. Koski, Woodbury, N.J.

[73] Assignee: American Hospital Supply Corporation, Evanston, Ill.

[21] Appl. No.: 902,029

[22] Filed: May 2, 1978

[51] Int. Cl.$^2$ .................... C09K 3/00; G01N 31/22; G01N 33/16
[52] U.S. Cl. ................... 252/408; 23/230 R; 23/230 B; 422/61
[58] Field of Search ............ 23/230 R, 230 B; 252/408

[56] References Cited

U.S. PATENT DOCUMENTS

| 2,668,797 | 2/1954 | Jones et al. | 252/408 |
| 3,945,798 | 3/1976 | Young | 23/230 R |

OTHER PUBLICATIONS

Nauman, R. V., et al., Anal. Chem., vol. 32, No. 10, pp. 1307-1311 (1960).
Kramm, D. E., et al., Anal. Chem., vol. 27, No. 7, pp. 1076-1079 (1955).
Yoe, J. H., et al., Ind. Eng. Chem., Anal. Ed., vol. 13, No. 4, pp. 238-240 (1941).
Segal, L., Anal. Chem., vol. 23, No. 10, p. 1499 (1951).
Hoffpauir, C. L., et al., Ind. Eng. Chem., Anal. Ed., vol. 15, No. 9, pp. 605-606 (1943).
Blaedel, W. J., et al., Ind. Eng. Chem., Anal. Ed., vol. 13, No. 7, pp. 449-450 (1941).

*Primary Examiner*—Teddy S. Gron
*Attorney, Agent, or Firm*—Edward A. Figg; Robert E. Hartenberger

[57] ABSTRACT

A reagent for detection of aldehydes in biological specimens. The reagent is a modified Schiff reagent which is stable at room temperature for a substantial period of time. The reagent comprises potassium metabisulfite, pararosanilin acetate and hydrochloric acid. The potassium metabisulfite and pararosanilin acetate are included in the reagent in equal amounts. The sulfur dioxide source is potassium metabisulfite. The pH of the reagent ranges from about 1.2 to about 2.7.

5 Claims, No Drawings

STABLE SCHIFF REAGENT

BACKGROUND OF THE INVENTION

This invention relates to Schiff reagents and, more particularly, to a Schiff reagent which is stable at room temperature.

The Schiff reagent, a well-known reagent, is a complex organic molecule which is specific for aldehydes generated in biological specimens.

The Schiff reagent was first formulated by the German chemist Hugo Schiff as a qualitative test for aldehydes in 1865; rosanilin, a magenta colored dye, was converted to a colorless (leuko) reagent by the addition of sulfur dioxide to an aqueous solution. The reagent became recolorized by the addition of compounds containing the aldehyde functional group.

The first biological application of the Schiff reagent was in 1924 by Feulgen and is known by his name. Feulgen used the reagent to detect aldehydes generated by acid hydrolysis of deoxyribose sugar of deoxyriboneucleic acid (DNA).

The Schiff reagent has always been known as an unstable reagent. As described in 1960 [Kasten, F. H. (1960): The Chemistry of Schiff Reagent, Intl. Rev. Cytol. 10:1–100.], the stability of the Schiff reagent ranges "from several hours to six months or longer, depending on the ingredients and the method of storing". The greatest longevity described was 13 months when the reagent was stored in a brown stoppered bottle in the refrigerator.

The stability of the reagent is directly affected by the loss (by evaporation) of $SO_2$ from the reagent. Where the loss of $SO_2$ is great and at a fast rate, the stability of the reagent decreases until it deteriorates and is of no use.

Accordingly, various methods have been employed to prevent the loss of $SO_2$. Two obvious methods were by storing the reagent in a stoppered bottle and at a low temperature. Evaporation of the $SO_2$ was also minimized by covering the surface of the reagent with xylene or mineral oil.

All of these methods have assisted in the control of the loss of $SO_2$. However there is still a need to maintain the level of $SO_2$ in the reagent and thus the stability of the reagent for a substantial period of time.

The present invention, as described below, satisfies this need by providing a sensitive reagent which is stable for a substantial period of time.

SUMMARY OF THE INVENTION

The present invention provides a sensitive Schiff reagent which is stable at room temperature for a substantial period of time. The reagent comprises potassium metabisulfite, pararosanilin acetate and hydrochloric acid. The potassium metabisulfite and the pararosanilin acetate are present in the reagent in equal amounts. The pH of the reagent ranges from about 1.2 to about 2.7. The period of time for which the reagent is stable at room temperature is at least about 18 months.

The Schiff reagent, according to the present invention, is combined with a periodic acid solution, a counterstain solution, and a sodium carbonate solution to make up a histochemical reaction set. The reaction set is sensitive and stable at room temperature for a period of at least about 12 months.

DESCRIPTION OF PREFERRED EMBODIMENTS

The present reagent is a variation of the Schiff reagent used for the histochemical and cytochemical detection of aldehydes in biological specimens. The reagent, as modified according to the present invention, remains stable and sensitive when stored at room temperature over a substantial period of time. The reagent has been found to be stable for a period of time of at least about 18 months.

The stability of the reagent is generally maintained by controlling the loss of sulfur dioxide ($SO_2$) by evaporation. A loss of $SO_2$ by evaporation tends to raise the pH of the reagent, while a decrease in the bisulfite due to oxidation tends to lower the pH. The pH of the reagent for best results ranges from about 1.2 to about 2.7. The pH of the present reagent has been found to remain constant for a period of over one year.

The sensitivity and stability of the reagent is primarily dependent upon the sulfur dioxide ($SO_2$) concentration. As a gas, sulfur dioxide is more soluble in cold solutions than in warm solutions. The sulfur dioxide, however, maintains an equilibrium in solution when the headspace (i.e., empty volume in the reagent container above the reagent level) is limited. In the present reagent there is negligible change of sulfur dioxide concentration in the unopened bottle when maintained at a temperature of 15°–30° C. over a period of at least one year.

When the reagent container has been opened, the rate of evolution of $SO_2$ gas is determined by (1) the temperature at which it is stored, and (2) the volume of headspace which exists in the reagent container. It has been found that where the reagent has been stored at higher temperatures, i.e., 37° C. and 56° C., the working shelf life will deteriorate rapidly. However, at room temperature, the $SO_2$ concentration decreases gradually, thus increasing the sensitivity of the reagent over a period of time of at least about 6 months.

The Schiff reagent, according to the present invention, is prepared with sulfurous acid-bisulfite, i.e., potassium metabisulfite, in the presence of HCl. As shown below, in the initial reaction with pararosanilin-acetate (parafuschsin), the sulfite is added to the central (triphenyl methyl) carbon atom with the loss of the quinoid structure:

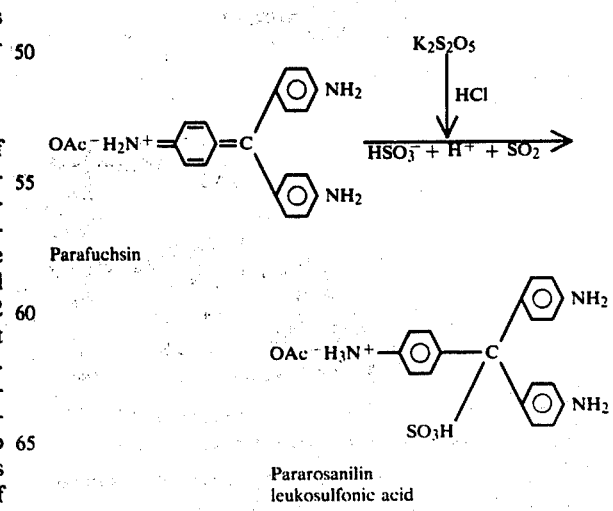

Parafuchsin

Pararosanilin leukosulfonic acid

Then, as illustrated below, the intermediate compound (pararosanilin leukosulfonic acid) is immediately converted to the N,N-disulfinic acid derivative to form the active Schiff reagent.

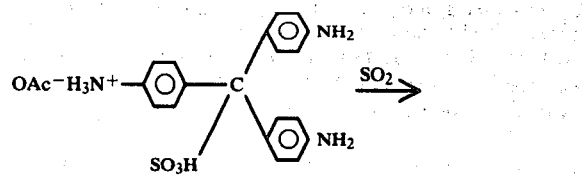

Pararosanilin leukosulfonic acid

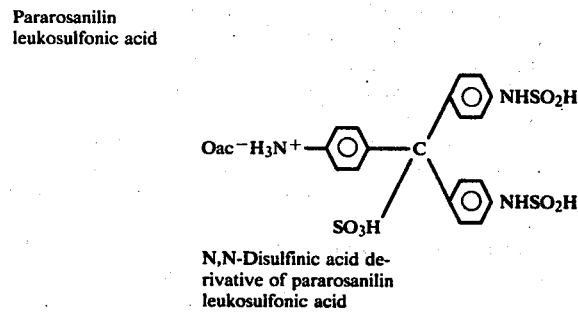

N,N-Disulfinic acid derivative of pararosanilin leukosulfonic acid

The active reagent, the N,N-disulfinic acid derivative of pararosanilin leukosulfonic acid, condenses with a variety of carbonyl compounds. It is believed that the carbonyl or aldehydes is the only species of significant quantity generated in biological specimens which reacts with the Schiff reagent.

The condensation product between the Schiff reagent and aldehydes is initially colorless, a slight pink tint being attributed to the loss of sulfur dioxide from the reagent to the atmosphere:

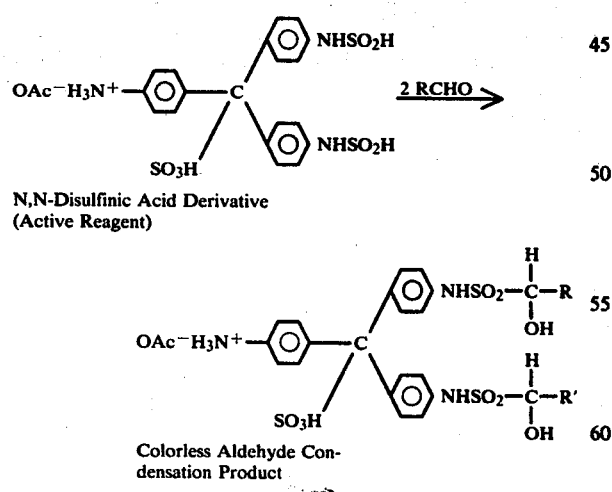

N,N-Disulfinic Acid Derivative (Active Reagent)

Colorless Aldehyde Condensation Product

The color of the dye molecule is restored with simultaneous restoration of the quinoid structure by transformation of the complex through loss of sulfurous acid by neutralization with aqueous sodium carbonate:

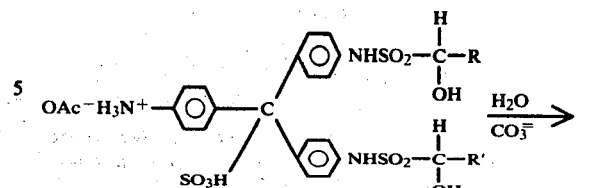

Colorless Aldehyde Condensation Product

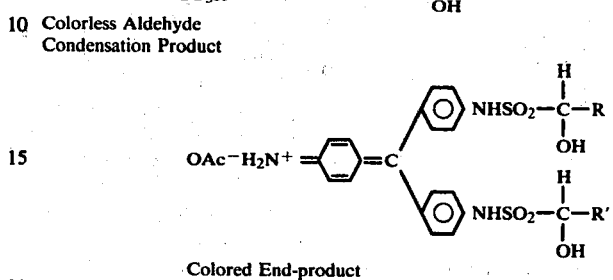

Colored End-product

As demonstrated in the reaction above, the acetate anion is in equilibrium with the free hydrogen ion. Thus, by tying up the hydrogen ion with the acetate, it is possible to decrease the rate of evolution of sulfur dioxide. This rate phenomenon occurs since hydrogen is able to readily recombine with the bisulfite ($HSO_3$) to form sulfurous acid which readily dissociates into water and sulfur dioxide gas which, in turn, is lost to the atmosphere.

The Schiff reagent, as described above, is used to demonstrate aldehydes in biological specimens such a membranes, tissues and the like. The potassium metabisulfite is added to the reagent in proportion to the pararosanilin acetate in a ratio of from about 1:1 to about 2:1. It is preferred, however, to have equal amonts of the bisulfite and parafuchsin in the reagent.

According to the present invention, the Schiff reagent may be used to make up a histochemical reaction set for the detection of carbohydrate moieties in biological specimens.

The reaction set consists of: (a) the Schiff reagent; (b) a periodic acid solution; (c) a counterstain, e.g., a light green SF yellowish solution or hematoxylin; and (d) a sodium carbonate solution.

The reaction set has a high sensitivity and is stable at room temperatures. The reaction set may be stored at room temperatures (15°-30° C.) for periods of 12 months and more. The Schiff reagent is stable, as well as the other components of the reaction set.

The sodium carbonate solution assures the alkalinity of the developer rinse, thus insuring full color development. A working sodium carbonate solution is prepared prior to use by diluting 2 ml. of sodium carbonate to 40 ml. with distilled or deionized water.

The following examples are provided to further illustrate the advantages of the present invention.

EXAMPLE 1

PREPARATION OF SCHIFF REAGENT

In the preparation of the Schiff reagent, the following materials, and amounts, were used:

| Material | Amount/Liter | Total Amount |
| --- | --- | --- |
| Parafuchsin | 4.55 gr. | 172.9 gr. |
| HCl, normal | 86.5 ml. | 3.287 Liters |
| Potassium metabisulfite | 4.55 gr. | 172.9 gr. |
| Carbon, Nuchar XXX | 4.00 gr. | 152.0 gr. |

| -continued | | |
|---|---|---|
| Material | Amount/Liter | Total Amount |
| Water, deionized (for rinses) | 10 ml. | 380 ml. |
| Water, deionized (diluted to) | 910 ml. | 38 Liters |

Initially, approximately ⅔ of the total volume of deionized water was added to a suitable stock container. Then, to four (4) 12 liter boiling flasks, 10 liters of deionized water was added. The parafuchsin was divided into four (4) equal portions and added to each boiling flask. The flasks were heated to boiling and agitated to dissolve all the dye, i.e., the parafuchsin. Then the contents of the flasks were added to the stock container. Each of the flasks were rinsed, using 500 ml. of deionized water, and the washings were added to the stock container.

All of the HCl was then added to the stock container with the potassium metabisulfite. The contents were agitated to dissolve all the contents in the stock container. After the materials were dissolved, the remainder of the deionized water was added to the stock container to bring the level of the reagent to total volume. The container was sealed and allowed to stand in the dark overnight until the solution changed from a cherry red to a straw color.

The Nuchar carbon was added, and the mixture was stirred. The carbon was allowed to settle for one hour, and the mixture was immediately filtered through a Celite bed (12 gm.) into a stock container of equal size. The straw color was removed, and then approximately 50 ml. of the reagent was submitted to Quality Assurance (QA) for testing. The container was tightly stoppered until the reagent was properly packaged.

EXAMPLE 2

USE OF HISTOCHEMICAL REACTION SET

In demonstrating carbohydrate moities in biological specimens, the materials listed below were used. The stability of the Schiff reagent was assured by placing in a disposable tube 1 ml. of formalin solution (37–40%) with one drop of the reagent. A magenta color developed within 5 seconds, gradually turning to dark purple. This assured the quality and stability of the reagent.

In the demonstrations, a specimen of a tissue containing glycogen, intestinal mucin or fungus served as a previously proven positive control. The amount of each of the Schiff reagent, Periodic Acid Solution, Light Green SF Yellowish Solution and Sodium Carbonate Solution was 225 ml.

| MATERIALS |
|---|
| Schiff Reagent |
| Periodic Acid Solution |
| Light Green SF Yellowish Solution |
| Sodium Carbonate Solution |
| Disposable Tubes (not resistant to xylene or toluene) |
| Toluene |
| Absolute Alcohol |
| Forceps |
| Distilled water |
| Disposable pipettes - 4 per test to flood slides |
| Volumetric pipette - 2 ml. |
| Graduated cylinder - 50 ml. |
| Staining rack |
| Mounting Medium (Coverbond) |
| Microslides |
| Coverslips |
| Microscope |

| MATERIALS |
|---|
| Timer accurate to one minute |

Initially, the slides, having the biological specimen (e.g., tissue) mounted thereon, were deparaffinized to distilled water. Each slide was then flooded with the Periodic Acid and allowed to stand for 10 minutes. Then, after being rinsed in distilled water, the slides were flooded with the Schiff reagent and allowed to stand for 15 minutes. Then, after each slide was rinsed in distilled water for one minute, the slides were flooded with the sodium carbonate working solution and allowed to stand for five minutes.

After being flooded with the carbonate solution, the slides were rinsed in distilled water, flooded with the Light Green SF yellowish solution and allowed to stand for 10 to 30 seconds. The slides were then rinsed briefly (i.e., for approximately 5–10 seconds) for just the necessary time to bleed the excess stain from the section of the slide. The sections were dehydrated with agitation in absolute alcohol for two changes of 10 seconds each. Then, after the slides were made clear in toluene, they were mounted with a Coverbond.

As a result of the use of reaction set, the carbohydrate groups and biological structures associated therewith were stained with a color of pink to magenta, and the background material is stained green. If the hematoxylin was used as a counterstain, the nuclei stain would have a color of from purple to blue.

In the process outlined above, the flooding of the slides was done to inhibit the loss of sulfur dioxide ($SO_2$) from the Schiff reagent and to ensure the chemical integrity of all the reagents and components of the histochemical reaction set.

EXAMPLE 3

STABILITY STUDY OF HISTOCHEMICAL REACTION SET

The reagent set was tested for its ability to withstand temperature variations in shipping and long-term storage to substantiate its stability and sensitivity for use in the demonstration of carbohydrate moities in biological specimens. The stability of the Schiff reagent has been determined by both the pH of the reagent and the performance of the reagent. The stability and performance of the Schiff reagent is directly related to the loss of $SO_2$ therefrom, and the loss of $SO_2$ raises the pH. The stability of the reagent is lessened with the loss of $SO_2$ by evaporation and into the headspace (space above level of reagent in bottle) of the reagent bottle.

In the tests, 18 reagent sets were stored at the following temperatures: 4° C., room temperature (R.T.) and 37° C. The pH of the Schiff reagent of the reaction sets are recorded below for the various temperatures (i.e., 4° C., room temperature-R.T., and 37° C.) for the time periods from the initial time to 18 months.

| Schiff Reagent pH At Various Temperatures And Time Periods | | |
|---|---|---|
| Time Period | Temperature | pH |
| Initial | R.T. | 1.511 |
| 2 months | 4° C. | 1.446 |
| " | R.T. | 1.393 |
| " | 37° C. | 1.414 |
| 4 months | 4° C. | 1.715 |

Schiff Reagent pH At Various Temperatures And Time Periods

| Time Period | Temperature | pH |
|---|---|---|
| " | R.T. | 1.727 |
| " | 37° C. | 1.603 |
| 6 months | 4° C. | 1.500 |
| " | R.T. | 1.460 |
| " | 37° C. | 1.470 |
| 10 months | 4° C. | 1.529 |
| " | R.T. | 1.433 |
| " | 37° C. | 1.412 |
| 12 months | 4° C. | 1.414 |
| " | R.T. | 1.410 |
| " | 37° C. | 1.387 |
| 15 months | 4° C. | 1.247 |
| " | R.T. | 1.343 |
| " | 37° C. | 1.340 |
| 18 months | 4° C. | 1.445 |
| " | R.T. | 1.432 |
| " | 37° C. | 1.434 |

From the above pH data, the $SO_2$ content of the Schiff reagent and the performance of the Schiff reagent with the other reagents, the histochemical reagent set is certainly stable and sensitive when stored at room temperature and for a period of at least up to one year. By maintaining the $SO_2$ content of the Schiff reagent and avoiding the rapid evaporation therefrom, the Schiff reagent, as well as the reaction set, remain stable at room temperature for a substantial period of time.

We claim:

1. A sensitive reagent for detection of aldehydes in biological specimens, which reagent is stable at room temperature for a substantial period of time, comprising potassium metabisulfite, pararosanilin acetate and hydrochloric acid, and having a pH of from about 1.2 to about 2.7.

2. A reagent according to claim 1, wherein equal amounts of said potassium metabisulfite and pararosanilin acetate are present.

3. A reagent according to claim 1, wherein said acetate stabilizes the solution.

4. A reagent according to claim 1, wherein said period of time is at least about 18 months.

5. A reagent according to claim 1, wherein said room temperature ranges from about 15° C. to about 30° C.

* * * * *